United States Patent
Nixon

(10) Patent No.: US 12,193,900 B2
(45) Date of Patent: Jan. 14, 2025

(54) DENTAL STONE POWDER AND FIBER REINFORCED DENTAL STONE COMPRISING THE SAME

(71) Applicant: Ransom & Randolph LLC, Maumee, OH (US)

(72) Inventor: Daniel Paul Nixon, Monclova, OH (US)

(73) Assignee: Ransom & Randolph LLC, Maumee, OH (US)

( * ) Notice: Subject to any disclaimer, the term of this patent is extended or adjusted under 35 U.S.C. 154(b) by 240 days.

(21) Appl. No.: 17/568,869

(22) Filed: Jan. 5, 2022

(65) Prior Publication Data

US 2022/0313403 A1    Oct. 6, 2022

Related U.S. Application Data

(60) Provisional application No. 63/169,448, filed on Apr. 1, 2021.

(51) Int. Cl.

| | |
|---|---|
| *A61C 13/34* | (2006.01) |
| *A61K 6/73* | (2020.01) |
| *A61K 6/78* | (2020.01) |
| *A61K 6/831* | (2020.01) |
| *A61K 6/836* | (2020.01) |
| *A61K 6/889* | (2020.01) |

(52) U.S. Cl.
CPC .............. *A61C 13/34* (2013.01); *A61K 6/73* (2020.01); *A61K 6/78* (2020.01); *A61K 6/831* (2020.01); *A61K 6/836* (2020.01); *A61K 6/889* (2020.01); *A61C 2201/002* (2013.01)

(58) Field of Classification Search
CPC . A61K 6/73; A61K 6/78; A61K 6/858; A61K 6/871
See application file for complete search history.

(56) References Cited

U.S. PATENT DOCUMENTS

| | | | | |
|---|---|---|---|---|
| 3,047,408 | A * | 7/1962 | Dougherty | A61K 6/889 106/35 |
| 4,478,641 | A * | 10/1984 | Adair | C03B 32/02 106/38.3 |
| 4,604,142 | A * | 8/1986 | Kamohara | C04B 28/14 106/35 |
| 4,771,112 | A * | 9/1988 | Engelbrecht | C09J 4/06 528/96 |
| 4,806,381 | A * | 2/1989 | Engelbrecht | C08F 8/28 433/228.1 |
| 5,417,750 | A * | 5/1995 | Cohen | A61K 6/90 106/35 |
| 8,535,392 | B2 * | 9/2013 | Hong | C11D 3/40 8/647 |
| 2004/0002037 | A1* | 1/2004 | Orlowski | C08F 265/06 433/220 |
| 2004/0053200 | A1* | 3/2004 | Kato | A61C 13/20 264/16 |

(Continued)

*Primary Examiner* — Andrew D Graham
(74) *Attorney, Agent, or Firm* — Frost Brown Todd LLP

(57) ABSTRACT

Fibers, for example fiberglass fibers, are added to dental stone powders to provide for reinforced dental stones. Dental stones are made by combining dry components, including binder and fiber glass, adding water to the resulting mixture and setting the mixture in a dental mold. The dental stones are reinforced by the fibers, and allow for reduced breaking or chipping during handling.

15 Claims, 2 Drawing Sheets

(56) References Cited

U.S. PATENT DOCUMENTS

| | | | |
|---|---|---|---|
| 2004/0192804 A1* | 9/2004 | Kura | C08F 2/50 430/920 |
| 2006/0194895 A1* | 8/2006 | Loveridge | A61K 6/887 523/115 |
| 2008/0004369 A1* | 1/2008 | Seppala | C08G 4/00 524/437 |
| 2009/0042166 A1* | 2/2009 | Craig | A61C 3/02 451/28 |
| 2009/0148813 A1* | 6/2009 | Sun | A61K 6/891 433/213 |
| 2010/0035210 A1* | 2/2010 | Suchan | A61C 13/0003 433/201.1 |
| 2010/0069527 A1* | 3/2010 | Arata | A61K 6/40 523/118 |
| 2010/0099058 A1* | 4/2010 | Wang | A61C 13/0004 433/201.1 |
| 2010/0239679 A1* | 9/2010 | Greene | A01N 25/10 424/490 |
| 2010/0261143 A1* | 10/2010 | Hampe | A61K 6/60 523/105 |
| 2011/0046262 A1* | 2/2011 | Bublewitz | A61K 6/18 523/121 |
| 2012/0093741 A1* | 4/2012 | Maletz | A61K 6/20 522/171 |
| 2013/0030080 A1* | 1/2013 | Kadobayashi | A61K 6/17 523/115 |
| 2013/0071814 A1* | 3/2013 | Boehner | A61C 5/70 427/2.29 |
| 2013/0172441 A1* | 7/2013 | Takahata | A61C 13/0022 523/115 |
| 2014/0083326 A1* | 3/2014 | Mori | A61K 6/858 106/35 |
| 2014/0295376 A1* | 10/2014 | Uchida | A61K 6/16 427/2.29 |
| 2014/0302459 A1* | 10/2014 | Wang | A61C 8/0068 433/201.1 |
| 2015/0050621 A1* | 2/2015 | Formby | A61C 5/50 433/226 |
| 2015/0202123 A1* | 7/2015 | Ishihara | A61K 6/76 523/116 |
| 2016/0250107 A1* | 9/2016 | Kita | A61K 6/78 523/115 |
| 2017/0007378 A1* | 1/2017 | Gyakushi | A61K 6/35 |
| 2017/0135910 A1* | 5/2017 | Kudo | A61K 6/887 |
| 2018/0214352 A1* | 8/2018 | Takahashi | A61K 6/887 |
| 2020/0347191 A1* | 11/2020 | Gomurashvili | A61K 6/824 |
| 2021/0015716 A1* | 1/2021 | Hong | A61K 6/62 |

* cited by examiner

DENTAL STONE POWDER AND FIBER REINFORCED DENTAL STONE COMPRISING THE SAME

CROSS-REFERENCE TO RELATED APPLICATION

This application claims priority to and the benefit of U.S. Patent Application No. 63/169,448, entitled "Dental Stone Powder and Fiber Reinforced Dental Stone Comprising the Same," which was filed on Apr. 1, 2021. The contents of the aforementioned application are incorporated herein in their entirety for all purposes.

BACKGROUND

A dental stone model includes a replica of a person's teeth and gums that is generally used in dentistry for the production of dental prosthetics (e.g., bridges, crowns, implants, dentures, partial dentures, etc.). Such dental stone models are subject to various handling requirements and require sufficient strength to allow manipulation of the dental stone model without breaking or chipping. Dental stone models are typically formed by pouring a dental stone mixture into an impression mold and allowing it to harden (i.e., "set"). In many instances, to prevent breaking or chipping of the dental stone model, pins are placed in the dental stone model while the dental stone mixture is being poured into the impression mold to stabilize the model. This can increase the amount of time and costs for making the dental stone model. Moreover, if a dental stone model breaks, a new dental stone model would need to be created, which can also increase the amount of time and costs for making the dental stone model.

For the foregoing reasons, there remains a need for dental stone models comprising a reinforcing material to provide a strengthened dental stone model, which may inhibit breaking or chipping of the dental stone model during handling of the dental stone model to produce a dental prosthesis.

BRIEF DESCRIPTION OF THE DRAWINGS

It is believed the present invention will be better understood from the following description of certain examples taken in conjunction with the accompanying drawings.

Figure 1:
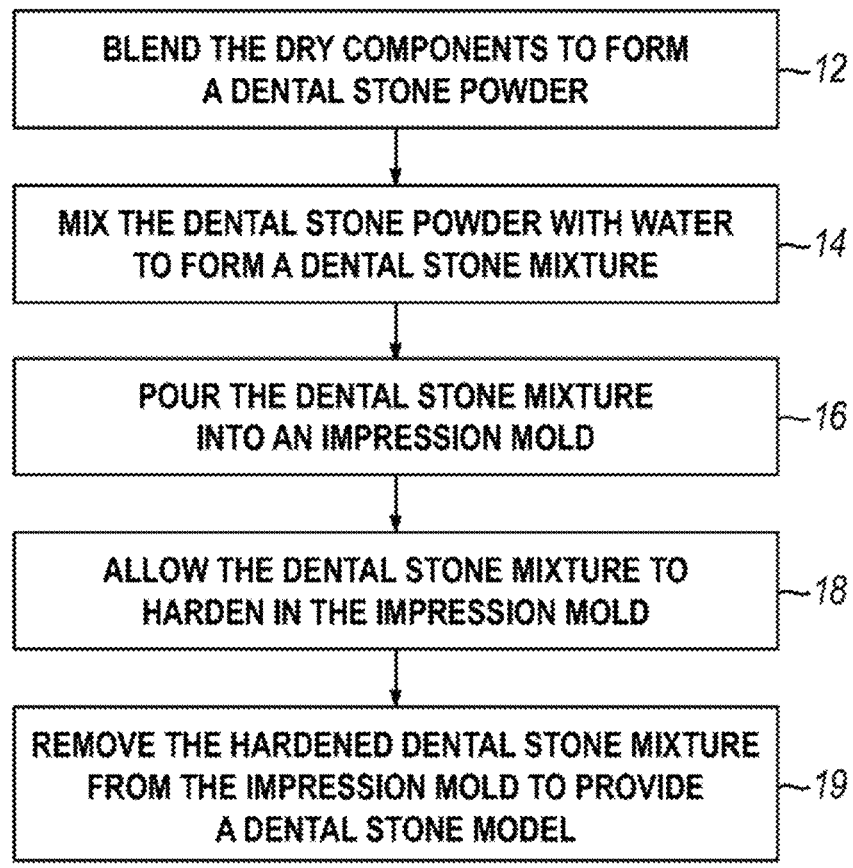
FIG. 1 depicts a flowchart of an exemplary method of making a fiber reinforced dental stone material.

The drawings are not intended to be limiting in any way, and it is contemplated that various embodiments of the invention may be carried out in a variety of other ways, including those not necessarily depicted in the drawing. The accompanying drawing that is incorporated in and forms a part of the specification illustrates several aspects of the present invention, and together with the description serves to explain the principles of the invention.

DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

All references, including patent applications, patent publications and non-patent literature, that are referred to in the present specification are incorporated by reference herein, unless it is expressly indicated that they are not incorporated by reference herein.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9 and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made. The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

As used herein, the terms "about" or "approximately" mean within an acceptable error range for the particular value as determined by one of ordinary skill in the art, which will depend in part on how the value is measured or determined, e.g., the limitations of the measurement system. Where particular values are described in the application and claims, unless otherwise stated the term "about" meaning within an acceptable error range for the particular value should be assumed. As used herein, the term "comprising" means that the various components, ingredients, or steps, can be conjointly employed in practicing the present invention. Accordingly, the term "comprising" encompasses the more restrictive terms "consisting essentially of" and "consisting of."

A dental stone powder in accordance with the present disclosure comprises one or more fibers to provide for a strengthened dental stone model (20). For instance, fibers can be homogeneously mixed with other components to generate dental stone powders in accordance with the present disclosure. The exemplary dental stone powders may be used to create a dental stone model (20) in which one or more bonds selected from mechanical bonds, covalent bonds, ionic bonds, Vander Waal forces and combinations thereof, may be formed between the fibers and one or more of the other components within the dental stone model (20). The one or more bonds may inhibit breaking or chipping of the dental stone model (20) during handling of the dental stone model (20), for example when producing a dental prosthesis. Accordingly, the number of pins that would otherwise be needed and/or the number of dental stone models (20) that would potentially need to be remade, may be reduced. Thus, utilizing exemplary dental stone powders to make dental stone models (20) in accordance with the present disclosure may advantageously decrease the time and costs typically associated with making dental stone models (20).

Components:

Exemplary dental stone powders comprise one or more fibers. More specifically, exemplary dental stone powders may comprise one or more fibers combined with components selected from: binders, fillers, plasticizers, pigments, and mixtures thereof.

Exemplary fibers of use may be selected from: organic fibers, inorganic fibers, and combinations thereof. Some exemplary dental stone powders may comprise fiberglass fibers. Some exemplary fibers are "electrical grade fiberglass ("E-glass") fibers having filament diameters that range from about 3 μm to about 20 μm. Some exemplary E-glass fibers range in length from about 2 mm to about 10 mm. Some exemplary E-glass fibers comprise around 80% by weight $SiO^2$ (silica). Some exemplary dental stone powders comprise from about 0.01% to about 1% of E-glass fibers.

Exemplary binders of use may be selected from alkali metal sulfates. Some exemplary dental stone powders comprise calcium sulfate. Some exemplary dental stone powders comprise from about 80% to about 99.99% of calcium sulfate.

Exemplary fillers are minerals including, but not limited to those that are known as refractory materials in the science of dentistry. Exemplary refractory materials of use may be selected from: quartz, feldspar, fused silica, kaolin, and mixtures thereof. Some exemplary dental stone powders comprise quartz. Some exemplary dental stone powders comprise from about 0% to about 20% of quartz, or greater than 0% and less than or equal to 20% of quartz.

Exemplary plasticizers of use may include dispersible polymeric powders. Exemplary dispersible polymeric powders may be selected from a powder comprising: polyvinyl acetate-polyethylene copolymer ("PVA-PE copolymer"), polyvinyl alcohol, polyethylene, and mixtures thereof. Useful dispersible polymeric powders include Vinnapas® 5010 N and Vinnapas® 5115 L (Wacker Chemie AG). Some exemplary dental stone powders may comprise PVA-PE copolymer. Some exemplary dental stone powders comprise from about 0% to about 5% of PVA-PE copolymer, or greater than 0% and less than or equal to 5% of PVA-PE copolymer.

Exemplary pigments of use may be selected from inorganic pigments, organic pigments, and mixtures thereof. Some exemplary dental stone powders comprise iron oxide pigment. Some exemplary dental stone powders comprise from about 0% to about 1% pigment, or greater than 0% and less than or equal to 1% pigment.

Some exemplary dental stone powders may comprise one or more of the following pigments in addition to, or in lieu of iron oxide pigment. Exemplary organic pigments may be selected from: azo pigments (e.g., condensed and/or chelate azo pigments); thiazoles; polycyclic pigments (e.g., phthalocyanines; anthraquinones; quinacridones; thioindigoids; isoindolinones; and/or quinophthalones); and mixtures thereof. These and other useful organic pigments may be found in U.S. Pat. No. 8,535,392 (Hong, et al.). Exemplary inorganic pigments may be selected from: titanium dioxide; white extender pigments (e.g., calcium carbonate; calcium sulfate; china clays; diatomaceous silica; and mixtures thereof); black pigments (e.g., carbon black); iron-oxide earth pigments (e.g., hematite; hydroxide goethite; iron oxides; manganese oxides; and mixtures thereof); chromium pigments (e.g., chromium oxide); cadmium pigments; metallic pigments; iron blue; and mixtures thereof. Some exemplary dental stone powders may comprise organic pigment selected from: Pigment Blue 29; Direct Yellow 28; LX-8939 Permanent Aquamarine; Dark Violet LX-11400; Orcoperm AG Ultramarine Blue; and mixtures thereof. Some exemplary STPs comprise Orcoperm AG Ultramarine Blue.

Method of Making:

Referring to FIG. 1, an exemplary method (10) is shown for making a fiber reinforced dental stone model (20). Method (10) comprises a step (12) of blending the dry components to form a dental stone powder. For instance, the dry components comprise one or more fibers combined with components that, may be selected from: binders, fillers, plasticizers, pigments, and mixtures thereof. The dry components can be combined in a mixing vessel, such as a V-blender, a tumble blender, a ribbon mixer, and/or other suitable mixing vessel configured to mix the dry components. The components can be agitated in the mixing vessel until a sufficiently homogeneous powder is formed. Accordingly, the dental stone powder can be a free-flowing powder with a homogenous mixture of powder particles and fiber strands.

After the dental stone powder is formed, method (10) comprises a step (14) of mixing the dental stone powder with water to form a dental stone mixture. For instance, the dental stone powder can be mixed with water at a weight ratio of from about 1 to about 5 of water to powder. This mixture can be mixed by hand with a spatula until the dental stone powder is sufficiently mixed into the water. Method (10) then comprises a step (16) of pouring the dental stone mixture into an impression mold. An impression mold is a negative replica of a patient's mouth that can be formed by making an imprint of the patient's teeth and gums using one or more impression materials (e.g., alginates, waxes, silicones, putties, etc.). Accordingly, the dental stone mixture can be poured into the impression mold such that the dental stone mixture forms a replica of at least a portion of the patient's teeth and gums. Method (10) comprises a step (18) of allowing the dental stone mixture to harden (i.e., "set") in the impression mold and a step (19) of removing the hardened dental stone mixture from the impression mold to provide a dental stone model (20).

An exemplary dental stone model (20) can be made with any dental stone powder in accordance with the present disclosure including, but not limited to, a dental stone powder as described in Table 1:

TABLE 1

| Component | Quantity |
| --- | --- |
| Calcium Sulfate | 80% to 99.99% |
| Fiberglass | 0.01% to 1% |
| Quartz | ≥0% to 20% |
| Polyvinyl acetate Polyethylene copolymer | ≥0% to 5% |
| Iron oxide | ≥0% to 1% |

Figure 2:
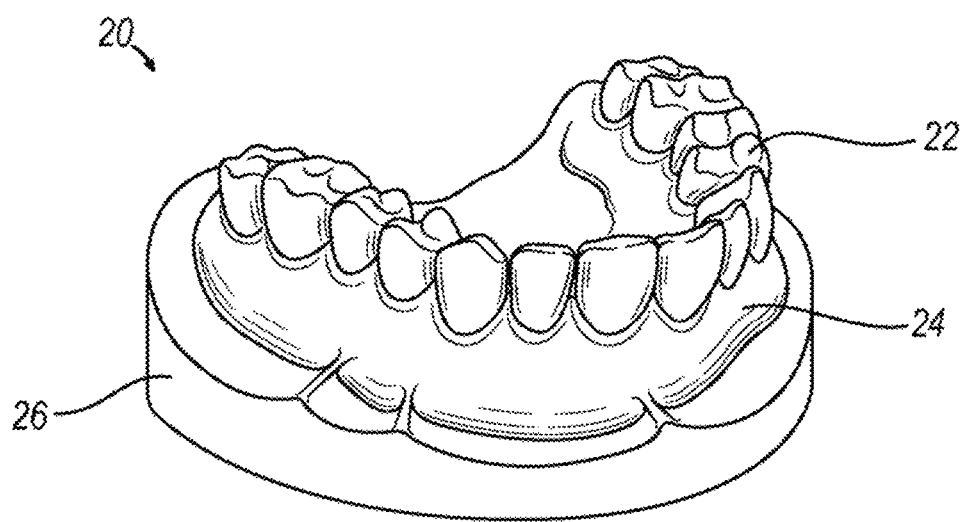
FIG. 2 depicts a prospective view of a dental stone model formed from an exemplary fiber reinforced dental stone material.

An exemplary dental stone model (20) as described herein is shown in FIG. 2 for illustrative purposes. Dental stone model (20) comprises at least a portion of a patient's teeth (22) and gums (24) coupled with a base (26). The dental stone model (20) formed by the dental stone material described herein can then be used for diagnostic purposes and/or to create dental prosthetics.

Applications:

The fiber reinforced dental stone powder as disclosed herein can be used to form any suitable dental gypsum product. For instance, dental gypsum is typically categorized into 5 types of products that can be used for dental purposes such as making oral impressions, molds, casts, dies or model bases, and/or mounting models. Types 1 and 2 typically refer to plasters that can be used for general applications, such as mounting models to articulators and/or for diagnostic models. Type 3 typically refers to model stone that can be used for dental stone models (20). Type 4 typically refers to a specialty or die stone. Type 5 typically refers to a high expansion die stone that can be used for a product having a loose or passive fit in the mouth. Each type of dental gypsum product can be classified based on requirements provided by the International Organization for Standardization (ISO) in ISO 6873 published in 2013. Such requirements are provided in Table 2 below.

TABLE 2

ISO 6873 Dental Stone Gypsum Specification

| Type | Setting Expansion (%) | Compressive Strength (psi) |
|---|---|---|
| 1 | 0.0-0.15% | 580-1,160 psi |
| 2 | 0.0-0.30% | 1,300 psi (minimum) |
| 3 | 0.0-0.20% | 2,900 psi (minimum) |
| 4 | 0.0-0.15% | 5,100 psi (minimum) |
| 5 | 0.16-0.30% | 5,100 psi (minimum) |

Setting expansion generally refers to an expansion of a peripheral boundary of a dental gypsum product when the product is mixed with water and allowed to set in air. In some versions, when additional water is brought into contact with the setting material, an increased expansion is observed. Compressive strength or compression strength is generally the capacity of a dental gypsum material to withstand loads tending to reduce its size.

Data:

A dental stone model (20) made with the fiber reinforced dental stone powder as disclosed herein has been found not to inhibit the ability of the dental stone model (20) to meet the ISO standard for each type of dental stone. For instance, a Type 4 dental stone model (20) made with the fiber reinforced dental stone powder as disclosed herein had a set expansion of 0.066% after a set time of 10.5 minutes and a compressive strength of 6,588 psi. Accordingly, the dental stone model (20) met and/or exceeded the ISO Type 4 dental gypsum requirements for set expansion and compressive strength.

While the fiber reinforced dental stone powder as described herein does not inhibit a compressive strength of a dental stone model (20) made with the fiber reinforced dental stone powder, such a dental stone model (20) can have improved tensile strength and shear strength. Tensile strength is generally the capacity of a dental gypsum material to withstand loads tending to elongate it. Shear strength is generally the capacity of a dental gypsum material to withstand loads tending to produce a sliding failure along a plane that is substantially parallel to the direction of the force. The fiber reinforced dental stone powder as described herein can also inhibit small cracks from propagating into larger cracks that result in model breakage. For instance, the Type 4 dental stone model (20) made with the fiber reinforced dental stone powder described above was also determined by an outside lab to have about 50% less model breakage relative to a dental stone model (20) without reinforcing fibers, which resulted in using about 50% less pins relative to a dental stone model (20) without reinforcing fibers.

I claim:

1. A dental stone powder comprising:
   (a) a binder, wherein the binder is calcium sulfate;
   (b) fibers selected from organic fibers, inorganic fibers and combinations thereof;
   (c) a filler;
   (d) a plasticizer; and
   (e) a pigment.

2. The dental stone powder of claim 2 claim 1, wherein the calcium sulfate is present at from about 80% to about 99.99% by weight of the dental stone powder.

3. The dental stone powder of claim 1, wherein the fibers comprise inorganic fiberglass fibers.

4. The dental stone powder of claim 3, wherein the inorganic fiberglass fibers are E-glass fibers having filament diameters that range from about 3 μm to about 20 μm.

5. The dental stone powder of claim 4, wherein the E-glass fibers are present at from about 0.01% to about 1% by weight of the dental stone powder.

6. The dental stone powder of claim 1, wherein the filler is quartz.

7. The dental stone powder of claim 6, wherein the quartz is present at greater than 0% and less than or equal to 20% by weight of the dental stone powder.

8. The dental stone powder of claim 1, wherein the plasticizer is a dispersible polymeric powder selected from a powder comprising: polyvinyl acetate-polyethylene copolymer (PVA-PE copolymer), polyvinyl alcohol, polyethylene and mixtures thereof.

9. The dental stone powder of claim 8, wherein the plasticizer is polyvinyl acetate-polyethylene copolymer (PVA-PE copolymer) that is present in the dental stone powder at from greater than 0% to less than or equal to 5% by weight of the dental stone powder.

10. The dental stone powder of claim 1, wherein the pigment is selected from inorganic pigments, organic pigments and combinations thereof.

11. The dental stone powder of claim 9, wherein the pigment is iron oxide that is present at greater than 0% and less than or equal to 1% by weight of the dental stone powder.

12. A dental stone powder model comprising
   (a) the dental stone powder of claim 1; and
   (b) water.

13. The dental stone powder model of claim 12, wherein the dental stone model is a Type 4 dental stone model that meets or exceeds ISO Type 4 dental gypsum requirements for set expansion and compressive strength.

14. The dental stone powder model of claim 12, wherein the dental stone model is a Type 4 dental stone model having a set expansion of 0.066% after a set time of 10.5 minutes and a compressive strength of 6,588 psi.

15. A dental stone powder consisting of:
   (a) from about 80% to about 99.99% calcium sulfate, by weight of the dental stone powder; and (b) inorganic glass fibers;
(c) quartz;
(d) a plasticizer; and
(e) a pigment selected from inorganic pigments, organic pigments and combinations thereof.

* * * * *